US007523755B2

(12) United States Patent
Richardson et al.

(10) Patent No.: US 7,523,755 B2
(45) Date of Patent: Apr. 28, 2009

(54) RESPIRATOR

(75) Inventors: Grant Stuart Richardson, Salisbury (GB); Alex Scott Rowbotham, Salisbury (GB); Graham Howell Williams, Salisbury (GB)

(73) Assignee: The Secretary of State for Defence (GB)

( * ) Notice: Subject to any disclaimer, the term of this patent is extended or adjusted under 35 U.S.C. 154(b) by 115 days.

(21) Appl. No.: 10/529,339

(22) PCT Filed: Sep. 29, 2003

(86) PCT No.: PCT/GB03/04207

§ 371 (c)(1),
(2), (4) Date: Sep. 16, 2005

(87) PCT Pub. No.: WO2004/028640

PCT Pub. Date: Apr. 8, 2004

(65) Prior Publication Data

US 2006/0118174 A1 Jun. 8, 2006

(30) Foreign Application Priority Data

Sep. 27, 2002 (GB) ................................ 0222497.0

(51) Int. Cl.

*A62B 18/10* (2006.01)
*A62B 18/02* (2006.01)
*A62B 9/02* (2006.01)
*A61M 16/00* (2006.01)

(52) U.S. Cl. ........................... 128/207.12; 128/201.28; 128/205.24; 128/205.25; 128/206.21; 128/204.18

(58) Field of Classification Search ............ 128/200.24, 128/201.26, 201.27, 201.28, 204.18, 204.22, 128/205.24, 205.25, 202.25, 206.15, 207.12; 137/240
See application file for complete search history.

(56) References Cited

U.S. PATENT DOCUMENTS

| | | | | |
|---|---|---|---|---|
| 3,633,611 | A * | 1/1972 | MacNiel | 137/494 |
| 3,680,555 | A * | 8/1972 | Warncke | 128/206.24 |
| 4,258,710 | A * | 3/1981 | Reber | 128/204.18 |
| 4,574,799 | A | 3/1986 | Warncke | |
| 4,608,976 | A * | 9/1986 | Suchy | 128/204.26 |
| 5,215,286 | A * | 6/1993 | Kolenc | 251/58 |
| 5,769,388 | A * | 6/1998 | Welker | 251/118 |

(Continued)

FOREIGN PATENT DOCUMENTS

DE 1181554 5/1958

(Continued)

*Primary Examiner*—Justine R Yu
*Assistant Examiner*—Annette F Dixon
(74) *Attorney, Agent, or Firm*—Dean W. Russell; Kilpatrick Stockton LLP

(57) ABSTRACT

A valve assembly (20) for a respirator comprises a valve body (25) having a valve outlet portion and a valve inlet portion which together define a valve cavity (30) for a valve mechanism (24) permitting gas flow from the valve inlet portion to the valve portion member, an air purge means comprising a purge inlet, connectable to an air pressure supply means, an air purge outlet (27) and an air deflection means (28) in which the deflection means is spatially arranged relative to the valve mechanism and purge outlet so that, in use, air exiting the purge outlet and incident the air deflection means provides a curtain of air over the valve mechanism.

14 Claims, 6 Drawing Sheets

U.S. PATENT DOCUMENTS

| | | | | |
|---|---|---|---|---|
| 6,729,331 | B2 * | 5/2004 | Kay | 128/205.24 |
| 7,013,891 | B2 * | 3/2006 | Richardson et al. | 128/201.15 |

FOREIGN PATENT DOCUMENTS

| | | |
|---|---|---|
| FR | 1399459 | 4/1965 |
| GB | 1139216 | 1/1969 |
| GB | 1587812 | 4/1981 |
| WO | WO 02/11816 | 2/2002 |

* cited by examiner

RESPIRATOR

CROSS REFERENCE TO RELATED APPLICATIONS

This application is the U.S. national phase of International Application No. PCT/GB2003/004207 filed on Sep. 29, 2003 and published in English on Apr. 8, 2004 as International Publication No. WO 2004/028640 A1, which application claims priority to Great Britain Application No. 0222497.0 filed on Sep. 27, 2002, the contents of which are incorporated by reference herein.

FIELD OF THE INVENTION

The present invention relates to the field of respirators, particularly, but not exclusively, those used for protection against toxic chemical and biological agents.

BACKGROUND OF THE INVENTION

Respirators were first developed in response to the use of chemical warfare agents in the First World War. Nearly all respirators have several common features-a seal suitable for forming a seal against the face, thus providing a cavity into which air is inhaled via a filter that removes noxious materials from the inhaled air. The seal prevents ingress of ambient, potentially foul, air into the cavity and thus into the lungs of the wearer. Air is drawn into the cavity either by the negative pressure caused by inhalation of the wearer or by the use of a positive pressure exerted, for example, by a pump. The respirators also normally comprise some sort of eyepiece.

U.S. Pat. No. 4,574,799 and GB 1587812 describe a respirator comprising both an oronasal mask and an outer face-sealing mask, wherein, in use, the oronasal mask forms a seal around the oronasal region of the face of the wearer and defines a cavity between itself and the outer mask such that substantially no pressure difference forms between the ambient atmosphere and the cavity between the oronasal mask and the outer mask that would allow ingress of ambient air into the cavity formed between the seal of outer mask and face and allows for compensation in the drop in pressure during inhalation that may lead to ingress of unwanted material via disrupted seal.

WO 02/11816 discloses a dual cavity respirator similar to those described in U.S. Pat. No. 4,574,799 and GB 1587812. The respirator of WO 02/11816 also comprises an ocular mask in gaseous communication with the oronasal mask. The ocular mask protects the eyes against potential damage should foul air enter the cavity between the outer mask and the oronasal mask. However, several problems have been experienced with such a respirator. It is difficult to incorporate the seals of the ocular and oronasal masks into the relatively small area defined by the size of the face of the wearer and so construction of the respirator is relatively complex and expensive. Furthermore, it is difficult to develop a seal on the ocular mask that fits all users due to the large variation of head and face shapes.

The respirator of the present invention seeks to overcome some or all of these problems.

SUMMARY OF THE INVENTION

Accordingly, in a first aspect of the present invention, there is provided a respirator comprising a respirator facepiece, a first sealing means suitable for forming a seal on the face of a user so as to define a first cavity between the first sealing means, the respirator facepiece and an area of the user's face comprising the eyes, mouth and nose, a second sealing means suitable for forming a seal on the face of the user so as to define a second cavity, the second cavity being formed between a portion of the face of the user, the second sealing means, the first sealing means and optionally the respirator facepiece, a respirator air inlet for conducting inhaling air to the first cavity, a respirator air outlet for conducting exhaled air from the first cavity, and an air pressure supply means suitable for supplying pressurised air to the second cavity whereby in normal operation air is inhaled and exhaled solely through the first cavity and so substantially no air pressure differential exists between the ambient atmosphere and the second cavity which will allow ambient air to enter the second cavity.

In use, the respirator provides a positive pressure in the cavity between the breathing cavity and the ambient atmosphere such that, should the second sealing means fail, then the positive pressure in the outer cavity urges air away from the point of failure of the seal, thus reducing the likelihood of ingress of contaminant into the respirator.

The first and second sealing means may comprise discrete components, which are separate from each other. Preferably, however, they share a common portion.

In a second aspect of the present invention, therefore, there is provided a sealing piece for a respirator, the sealing piece comprising first and second portions, each comprising a substantially compliant material and each having a respective sealing surface suitable for engagement with the face of the user, the first and second portions being mutually connected by a third portion suitable for attachment to the surface of a respirator, the sealing piece further comprising a gas inlet for allowing, in use, the supply of pressurised gas to the cavity, and wherein the first and second portions are so shaped that, in use, the application of a positive pressure in the cavity does not cause seals to be broken.

The sealing means or sealing piece may be adapted for increasing sealing contact under the influence of the air pressure supply. For example, the first and/or second sealing means or portions may comprise a reverse reflex seal. In particular, the first and/or second sealing means or portions may be J or U shaped in cross section.

Alternatively, or additionally the first and/or second sealing means or portions may be associated with or include a respective bladder, inflatable by the air pressure supply, which urges the sealing surface in contact with the face. It will be understood that the bladder will be located at, adjacent or integral to the non-contacting surface of the sealing means.

In a particularly preferred embodiment the second sealing means or portion includes a bladder or is associated with a bladder.

It will be understood that the sealing piece of the second aspect may be used with the respirator of the first aspect of the present invention.

The respirator preferably also comprises at least one eyepiece and a means for directing inhaling air over said at least one eyepiece. The inhaling air helps to demist the eyepiece and/or prevent misting from occurring. The means for directing inhaling air over said at least one eyepiece may additionally be capable of directing some of the inhaling air directly to the oronasal region of the user. One such means comprises a baffle plate.

The respirator may further comprise exhaust deflection means capable of preventing exhaled air from contacting said at least one eyepiece. Exhaled air is warm, and unless inhibited, tends to rise over the eyepiece if the user's head is in an upright position. The exhaled air may be moisture-laden and could cause the eyepiece to mist. An exhaust deflection means is therefore of benefit to the user.

The exhaust deflection means may comprise a third sealing means that, in use, engages with the face of the user so as to form ocular and oronasal cavities, the third sealing means being provided with means for permitting gaseous flow from the oronasal cavity to the ocular cavity. The means for permitting gaseous flow from the oronasal cavity to the ocular cavity may take the form of a diffuser and/or merely passages in the third sealing means. The third sealing means should be arranged to allow airflow from the ocular cavity to the oronasal cavity.

It will be realised that, the first and second air inlets may advantageously share a common filter connection means and filter Accordingly, in a third aspect, the present invention provides a respirator comprising a first sealing means suitable for forming a seal on the face of the a user so as to form a first cavity, the first cavity containing the oro-nasal region of the user, a second sealing means suitable for forming a seal on the face of a user so as to form a second cavity, an air pressure supply means in gaseous communication with a first air inlet and capable, in use, of providing gas to the second cavity, thus forming the first gaseous pathway, a second gaseous inlet which, in use, is in gaseous communication with the first cavity, thus forming a second gaseous pathway, the first and second air inlets being located in a common filter connection means, wherein the filter connection means is connectable to a suitably adapted filter such that in use the first and second gaseous pathways are mutually isolated so that inhalation by the user does not substantially affect the pressure in the first gaseous pathway.

This arrangement provides clean inhaled air and clean air to be supplied by the air pressure supply means through one respirator connection without increasing the work to be done by the air pressure supply means.

In prior art dual cavity respirators, a first sealing means is used to generate a first cavity that contains the oro-nasal region of the user, while a sealing means is used to define a second cavity, usually a space between the first sealing means, the second sealing means, the face of the user and the main body of the respirator. An air pressure supply means such as a bellows or electrical pump is used to provide the second cavity with pressurised air. This maintains a positive pressure in relation to the ambient atmosphere and, in the event that the second sealing means fails, then air from inside the second cavity urges out to the ambient atmosphere, reducing the likelihood of ingress of contaminated ambient atmosphere. The air pressure supply means has been arranged so as to draw air from the clean air that is to be inhaled into the first cavity as shown in WO 02/11816.

This simple prior art system has the disadvantage that, on inhalation, the air pressure within the first cavity falls. The air pressure supply means is a constant volume pump that attempts to maintain a constant flow of air through a pump. A drop in pressure within the first cavity causes the pump to experience a drop in air pressure at the air intake of the pump, thus causing the pump to increase its work rate in order to try to maintain the constant flow of air into the second cavity. This reduces the battery life of the pump. Attempts were made to alleviate the problem of the respirator of the prior art. For example, the pump was arranged such that it would only function on exhalation of the user. However, this did not provide a satisfactory pressure in the second cavity throughout the whole breathing cycle of the user. In an alternative attempt to solve the problem of the prior art, the inlet to the pump was arranged to have a separate air intake and filter, divorced from the inhalation air pathway. The pump was provided with its own filter. While satisfactory in some respects, this embodiment requires two separate filters and does not provide a satisfactory solution to the problem associated with the prior art.

In a fourth aspect, the present invention also provides a filter for a respirator, the filter comprising an inlet for the intake of a gas to be filtered, the inlet being in a gaseous communication with a plurality of mutually discrete filtration zones, each filtration zone comprising a filtration material capable of removing unwanted species from the gas to be filtered wherein each filtration zone is in gaseous communication with an outlet, each outlet being in gaseous communication with only one filtration zone, the outlets being located in a common respirator connection means.

It is preferred that the first filtration zone is of a circular section and the second filtration zone is of an annular section, the first filtration zone fitting snugly with the second.

It is preferred that the third and fourth aspects are used with first and second aspects of the present invention.

In any case the air pressure supply means may be electrically operated. For example, in a preferred embodiment, the filter connection means may include safety interlock means so that the air pressure supply is not operable unless a suitably adapted filter is fitted.

Preferably, the safety interlock means comprises an electrical arrangement. Thus, one or more electrical contacts on the filter connection means may be provided for electrical communication with the air pressure supply means. The filter may also comprise one or more electrical contacts suitable for electrical communication with the contacts of the filter connection means so as to form a completed electrical circuit, thus permitting the air pressure supply to the respirator.

In the absence of the filter the air pressure supply means is left in an open circuit mode and thus the air pressure supply means cannot operate. This also prevents the operation of the air pressure supply means when an inappropriate filter is fitted to the respirator. The safety interlock may alternatively and additionally be mechanical.

The respirator of the present invention may advantageously include an improved valve assembly, which offers superior protection over valves of prior art respirators. The improved valve assembly utilises the suggestion of WO 02/11816 that a purging airflow around the base of a valve assembly can reduce the likelihood of ingress of contaminated and/or exhaled air.

In a fifth aspect, therefore, the present invention provides a valve assembly comprising a valve body having a valve assembly outlet and a valve assembly inlet, and a valve cavity therebetween, a valve mechanism for permitting gaseous flow through the valve assembly inlet into the valve cavity and to the valve assembly outlet, a continuous purge outlet means connectable to an air pressure supply means, an air deflation means spatially arranged in the valve cavity relative to the valve mechanism and the purge outlet means such that, on connection and activation of a suitable air pressure supply means, air is emitted from the purge outlet means and is incident on the air deflection means such that a curtain of air may be substantially maintained above the valve mechanism.

The valve assembly in this aspect of the present invention embodies the prior art concept by including a purge outlet means connectable to an air pressure supply means and air deflection means providing a curtain or air above the valve mechanism. The air deflection means prevents air from mixing in the immediate vicinity of the valve mechanism and thus causing potentially harmful turbulent flow.

For the avoidance of doubt, it is hereby stated that the air pressure supply means is not part of the valve assembly; the purge outlet is merely connectable to an air pressure supply means. Further, as used herein, the term a "curtain of air" means a substantially unidirectional flow at any given point in the flow path for as long as the air pressure supply means is functioning.

Preferably, the purge outlet is positioned away from the valve mechanism such that, in use, the pressure experienced in the valve cavity in the immediate vicinity of the valve mechanism does not cause the valve mechanism to allow air flow from the valve cavity through the valve inlet to the interior of the respirator.

The interior of the valve body is preferably provided with a cylindrical bore, with the valve assembly inlet being situated at or near one end of the bore. With the cylindrical bore, the purge outlet means conveniently comprises an annular outlet around the circumference of the bore. If the purge outlet means is of an annular shape, then it is also preferred that the air deflection means comprises a hollow or solid cylinder.

The purge outlet may be in gaseous communication with a manifold. Preferably, the manifold is of a sufficiently large volume to assist in the maintenance of a curtain of air above the valve mechanism.

The valve assembly may be provided with a plurality of outlet conduits, each outlet conduit providing a tortuous outlet path to the valve assembly outlet. The cross-section of the gaseous pathway defined by each conduit decreases nearer the valve assembly outlet. This causes acceleration of the gas away from the outlet. It is further preferred that the valve assembly comprises anti-swirl vanes that reduce the cyclonic motion of any air that may enter the valve assembly. The anti-swirl vanes preferably project substantially radically from the air deflection means.

The valve assembly may be used in a respirator according to or including any aspect of the present invention. Of course, it will be apparent that it may also be used in any respirator although a means of supplying pressurised air must also be provided.

BRIEF DESCRIPTION OF THE DRAWINGS

The present invention will now be described by way of example only with reference to the following drawings in which.

DETAILED DESCRIPTION

Figure 1:
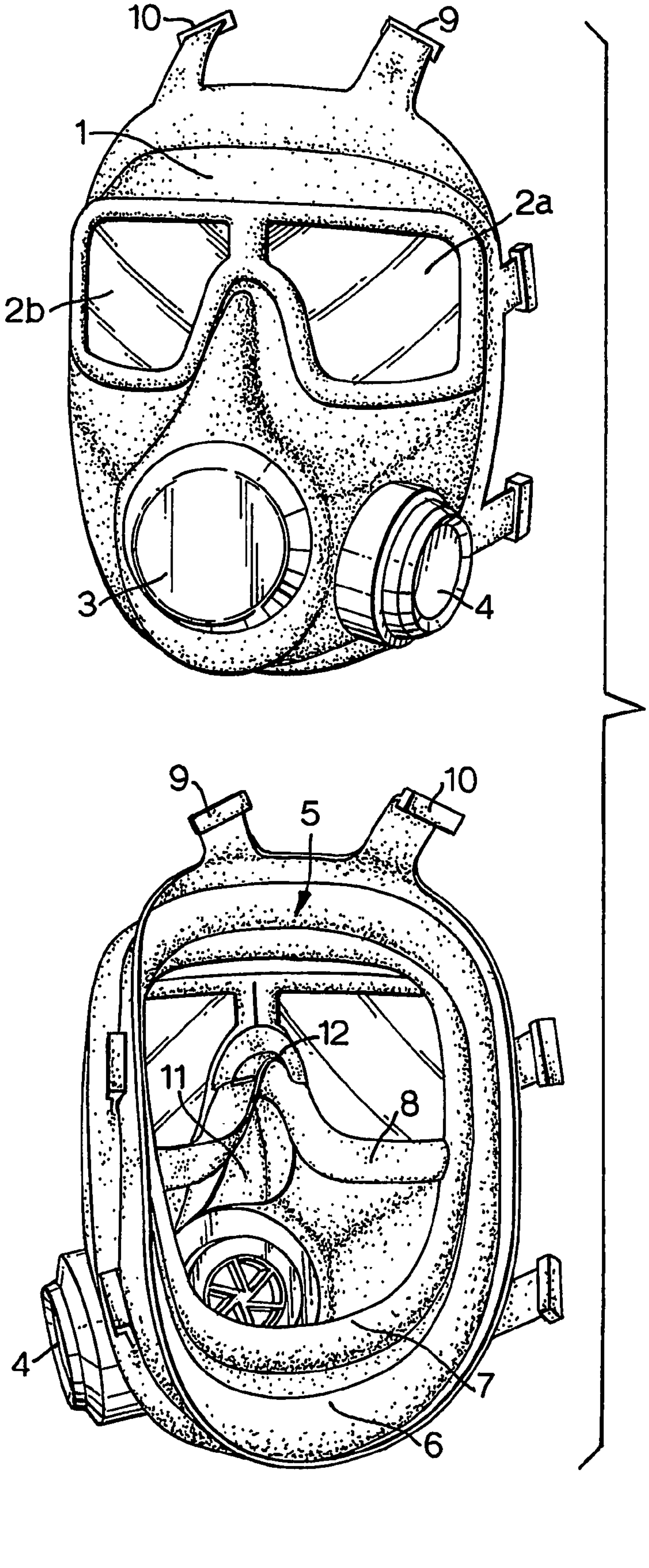
FIG. 1 shows an anterior and posterior view of a respirator in accordance with the first aspect of the present invention.

Referring now to FIG. 1 a respirator in accordance with the first aspect of the present invention comprises a facepiece 1, eyepieces 2*a* and 2*b*, air outlet 3, air inlet 4, first seal 7, second seal 6, exhaust deflection means 8, attachment lugs 9, 10, air guide 11, air pressure supply means (not shown) and diffuser 12.

In use, the respirator is placed on the face of the user. The first seal 7 forms a seal on the face around part of the face comprising the eyes, nose and mouth, such that a first cavity is formed between the first seal 7, the facepiece 1 of the respirator and the face of the user. The second seal 6 forms an outer seal around the first seal 7 such that a second cavity is formed, the second cavity being defined by the first and second seals and a portion of the face of the user. The air pressure supply means delivers pressurised air to the second cavity.

Air is inhaled and exhaled solely through air inlet 3 and air outlet 4 in the first cavity and so substantially no air pressure differential develops between the ambient atmosphere and the second cavity, which will allow ambient air to enter the second cavity.

The eyepieces 2*a* and 2*b* are made from transparent material and are placed in suitably sized cavities in the facepiece 1 to permit the wearer to see out of the respirator when in use. The eyepieces may be separate as shown in FIG. 1 or may be formed in one piece. The eyepieces 2*a*, 2*b* are sealed into the facepiece 1 to inhibit ingress of ambient gas through the join between the eyepieces 2*a*, 2*b* and the facepiece 1 into the interior of the respirator.

The exhaust deflection means 8 reduces the likelihood of warm, moisture-laden exhaled air from coming into contact with the eyepieces 2*a*, 2*b*. In this embodiment, the exhaust deflection means takes the form of a bar or strip of substantially compliant material that, in use, fits across the bridge of the nose and cheekbones of the user to substantially isolate the oronasal region of the user from the ocular region. The bar or strip is formed on the back of a substantially rigid skirt (not shown) that is attached to the facepiece of the respirator. The skirt allows air to pass from the oronasal region to the ocular region via diffuser 12. The bar or strip does not extend the whole width between the two sides of first seal 7. A small gap is formed between first seal 7 and the skirt to allow air to flow between the ocular region and the oronasal region. Not only does the exhaust deflection means 8 reduce the likelihood of exhaled air passing over the eyepieces 2*a*, 2*b*, but it also helps control the flow of demisting air over the eyepieces 2*a*, 2*b* and into the oronasal region.

In use, a filter (not shown) is mounted on the air inlet 4 and air is drawn through the air inlet 4 via the filter into the first cavity. Those skilled in the art will realise that the filter is not an essential element of this invention. Such filters are well known to those skilled in the art. Air may be drawn into the first cavity using negative or positive pressure. In a negative pressure respirator, the breathing action of the wearer reduces the air pressure in the first cavity relative to the ambient atmosphere. Air is then drawn through the air inlet from the ambient atmosphere (preferably through a filter) into the first cavity and then into the lungs of the wearer. In a positive pressure respirator, a pump or a fan (not shown) draw air into the first cavity to maintain a positive pressure therein.

Air drawn into the first cavity is directed by the air guide 11. The air guide 11 is a plastic duct attached to the facepiece 1 that diverts some of the inhaled air directly to the oronasal region of the user and some of the inhaled air to the gap in the exhaust deflection means to the diffuser 12. The air guide 11 may be arranged such that all inhaled air is initially directed to the diffuser 12 into the ocular region. The diffuser 12 causes the inhaled air to be passed over the eyepieces 2*a*, 2*b*. The inhaled air thus helps to keep the eyepieces free of mist or steam. The air then passes through the gaps between the first seal 7 and the exhaust deflection means back into the oronasal region to be inhaled by the user.

Exhaled air is exhausted to the ambient atmosphere via the air outlet 3. The air outlet 3 is fitted with a non-return valve and dead space (not shown) that inhibit ingress of contaminated air from the ambient atmosphere. Such valves and dead space arrangements are known to those skilled in the art.

During operation of the respirator, the air pressure supply means provides air to the second cavity (the cavity between the first and second seals) in order to maintain a positive pressure relative to the ambient atmosphere and thus reduce the likelihood of ingress of contaminated air into the second cavity.

Figure 2:
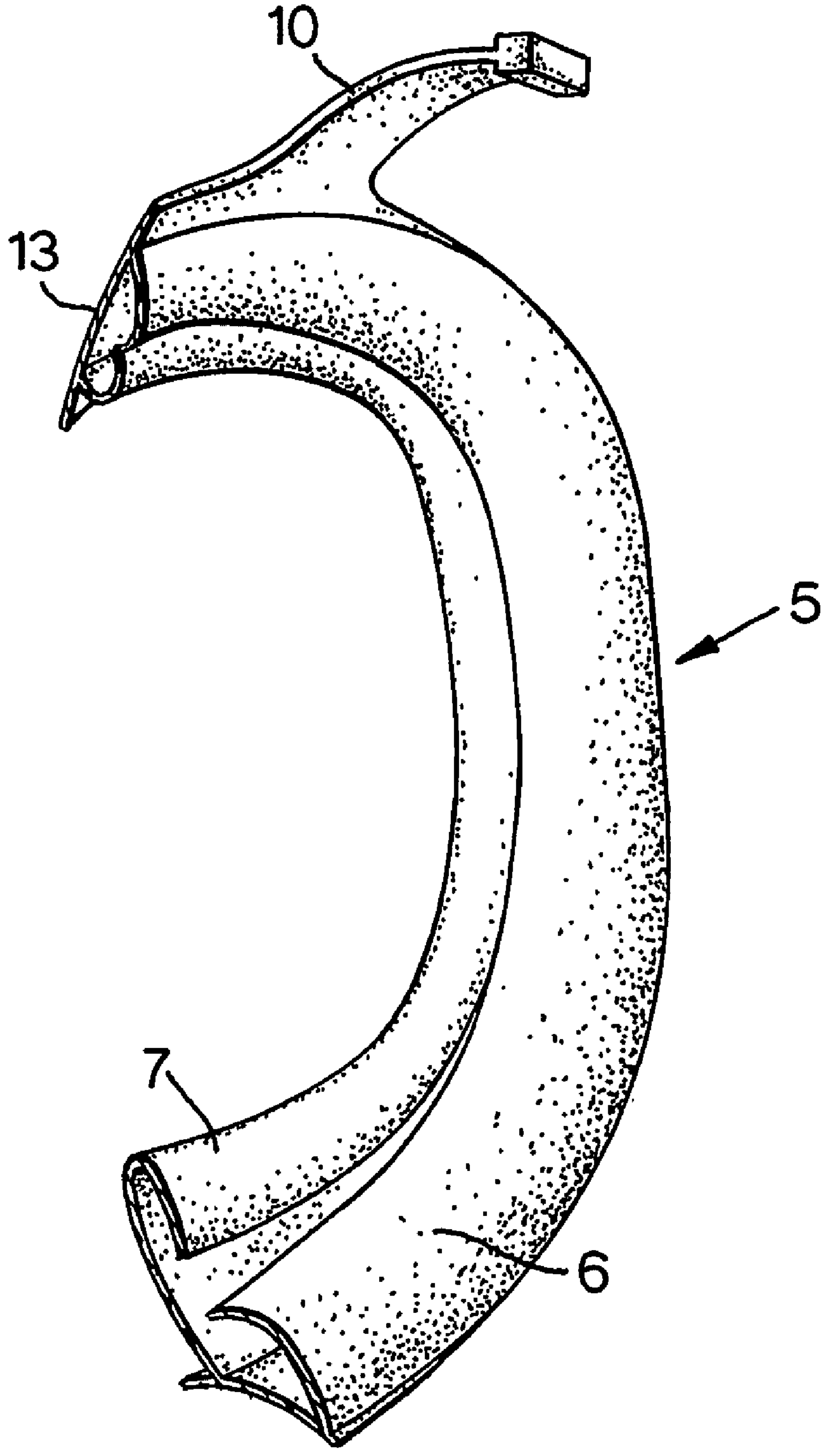
FIG. 2 shows a perspective view of a section of the sealing piece of FIG. 1, which illustrates the second aspect of the present invention.
Figure 3A:
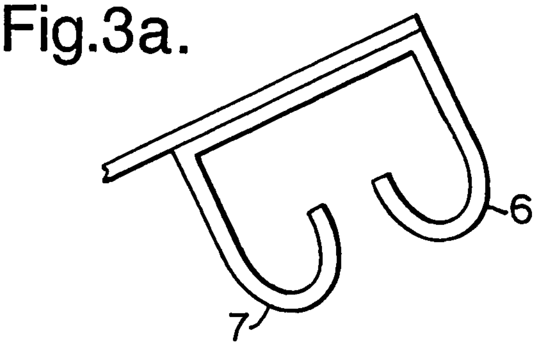
FIG. 3 shows a schematic representation of how the sealing piece of the present invention may be constructed with respect to a respirator.
Figure 3B:
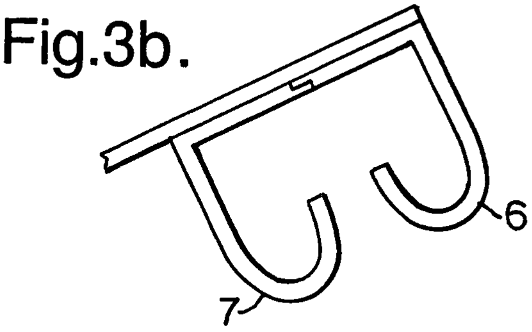
Figure 3C:
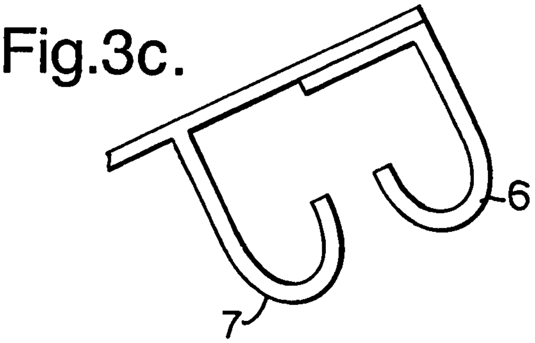
Figure 3D:
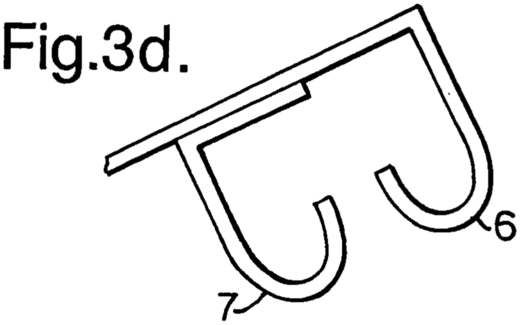

The sealing space 5 is shown in section in greater detail in FIG. 2 and comprises the first seal 7 connected tot he second seal 6 and attachment lugs 9, 10. The sealing piece 5 comprises first and second portions 7, 6 each comprising a substantially compliant material and each having a respective sealing surface suitable for engagement with the face of a user so as to define a substantially sealed cavity between the sealing piece and the face of the user, the first and second portions 7, 6 being connected by a third portion 13 suitable for attachment to the surface of a respirator, the sealing piece further comprising a gas inlet for allowing, in use, the supply of pressurised gas to the cavity, wherein the first and second portions are so shaped that, in use, the application of a positive pressure in the cavity does not cause the seals to be broken. First seal 7 and second seal 6 are linked by a connecting section the surface 13 of which may be attached to the body of the respirator. Straps (not shown) may be attached to the attachment lugs 9, 10 to enable snug fitting of the respirator to the head of the user.

FIG. 3 shows how the sealing piece of the present invention may be incorporated into a respirator. FIG. 3*a* shows that the second and first seals 6, 7 may be incorporated into a one-piece component. FIG. 3*b* shows that the seals 6, 7 may be separately attached to the body of the respirator. The one piece component 5 is advantageous, however, in that it allows both the first and second seal to be incorporated into a relatively small space, reduces production costs and complexity and allows simple relative position of the first and second seals. The one-piece sealing component 5 is, of course, made in one piece. FIGS. 3*c* and 3*d* show further alternative embodiments of the arrangement of seals 6, 7.

The first seal 7 is a reverse reflex seal whereas second seal 6 is a standard reflex seal. On the application of a positive pressure within the cavity between the seals 6, 7, then the second seal 6 is urged into greater engagement with the face of the user.

Figure 4:
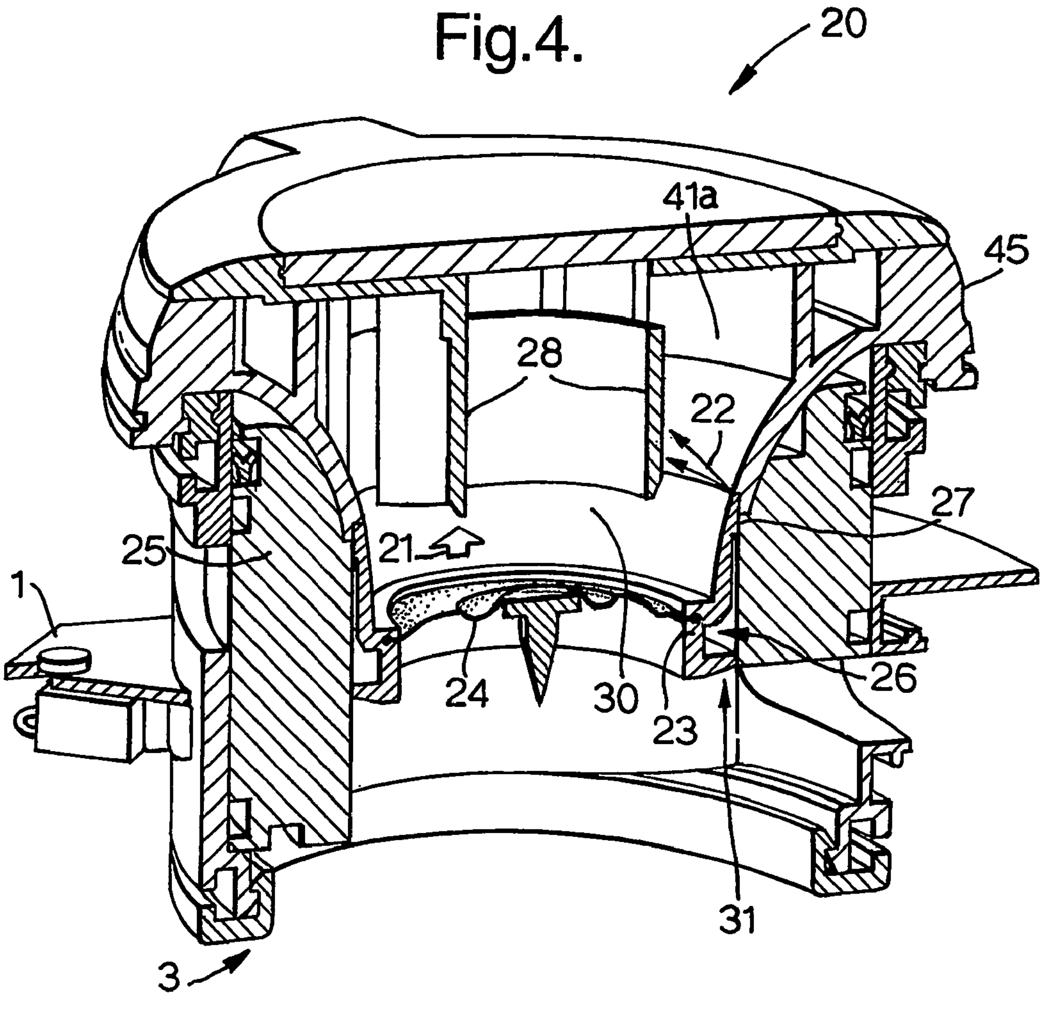
FIG. 4 shows a section through a valve assembly in accordance with the fifth aspect of the present invention.

Referring now to FIG. 4, a valve assembly 20 comprises a valve body 25 having a valve assembly outlet and a valve assembly inlet, and a valve cavity 30 therebetween, a unidirectional valve mechanism 24 for permitting gaseous flow through the valve assembly inlet into the valve cavity 30 and to the valve assembly outlet, a continuous purge outlet 27 connectable to an air pressure supply means, an air deflector 28 spatially arranged in the valve cavity 30 relative to the unidirectional valve mechanism 24 and the purge outlet 27 and is incident on the air deflector 28 such that a curtain of air 22 may be substantially maintained above the unidirectional valve mechanism 24.

A cylindrical bore has been formed in the valve body 25 to generate the valve cavity 30. The valve assembly 20 is shown located within a respirator air outlet 3 located within a respirator facepiece 1. In use, exhaled air 21 is driven through the unidirectional valve mechanism 24 that is located in the valve seat 23. The unidirectional valve mechanism 24 is typically a membrane. The unidirectional valve mechanism 24 inhibits flow of exhaled and ambient air through the valve assembly 20 into the respirator. A source of pressurised air, such as an air pump or bellows (not shown) is connected to the purge air inlet 31 that is in fluid communication with manifold 26. The manifold 26 is annular in shape and is in fluidic communication with purge outlet 27.

In use, the source of pressurised air provides pressurised air to the manifold 26. The pressurised air then passes to the purge outlet 27 that, in this case, is an annular shape. The outlet 27 is continuous around the circumference of the inner surface of the valve body 25. Air is urged from the purge outlet 27 in the form of a curtain of air 22 above the unidirectional valve mechanism 24. Such an arrangement inhibits the accumulation of exhaled air 21 or ambient air in the region of the unidirectional valve mechanism 24 and urges and potentially contaminated air away from the user, thus reducing the likelihood of any unwanted gas ingress into the respirator. The purge outlet 27 should not be positioned too close to the unidirectional valve mechanism 24 since moving air creates regions of low pressure adjacent to the moving air. If such a region of low pressure is too close to the unidirectional valve mechanism 24, then the membrane of the mechanism lifts, thereby permitting air in the proximity of the valve mechanism 24 to be breathed in by the user. The shape and size of the purge outlet 27 dictate the angle at which the air is emitted from the purge outlet 27. The air deflector 28 enables the formation of a curtain of air 22 above the unidirectional valve mechanism 24. After passing through the purge outlet 27, the air is directed onto the air deflector 28. The position, shape and size of the air deflector 28 are chosen so that there is no or little turbulent air flow in the air emitted through the purge outlet 27 in the region above the unidirectional valve mechanism 27. The curtain of air 22 is deflected by the air deflector 28 to conduit 41*a*. In the present case the air deflector 28 is cylindrical in shape.

Figure 5:
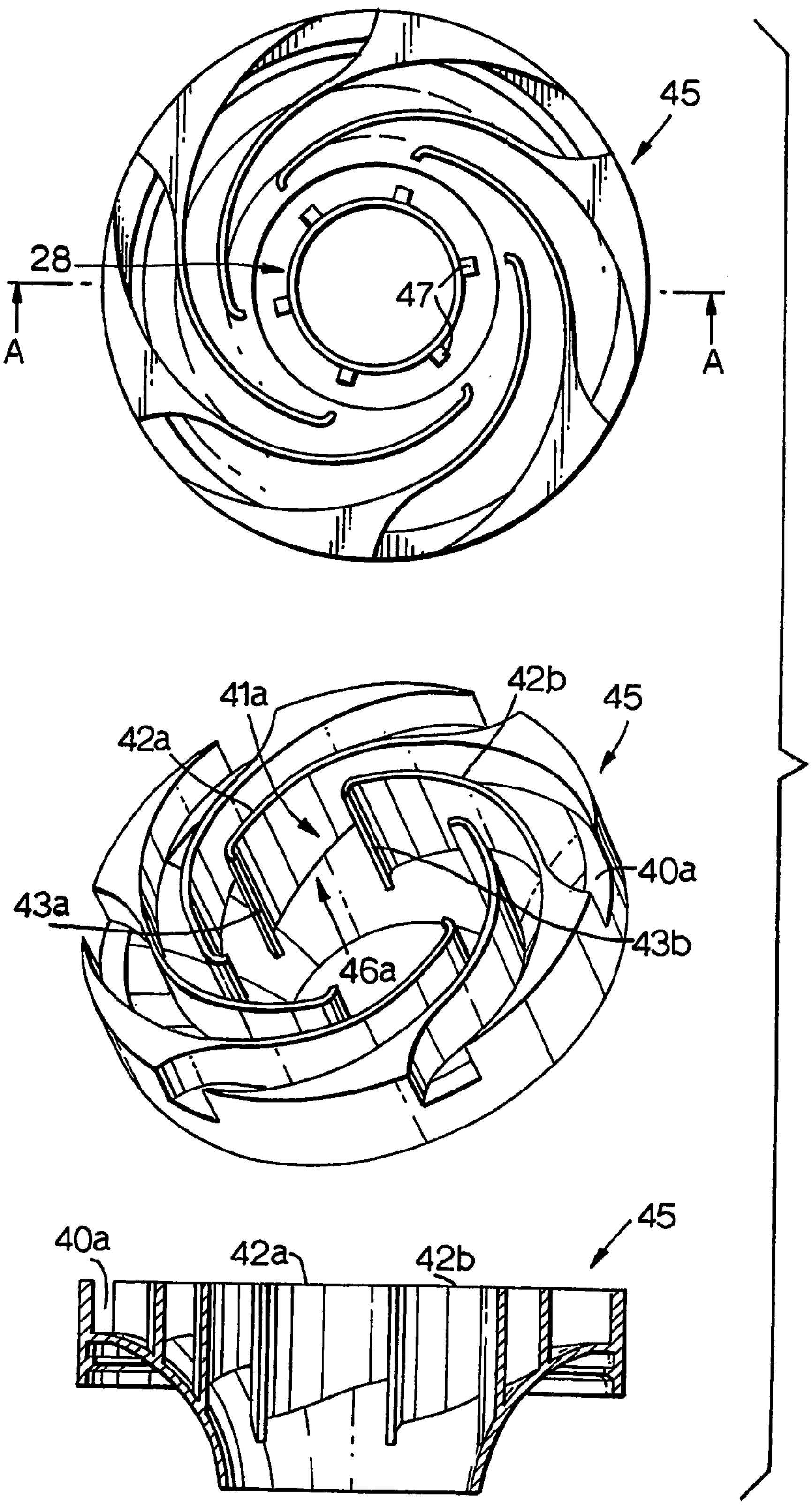
FIG. 5 shows a schematic representation of a component part of the valve assembly of FIG. 4.

The conduit 41*a* is one of six provided by a deadspace protection component 45 shown in detail in FIG. 5. The air deflector 28 is shown in FIG. 5 merely to illustrate the spatial relationship between the air deflector 28 and the deadspace protection component 45. The air deflector 28 is not part of the deadspace protection component 45. The six conduits are provided by a series of 6 guide walls. For clarity and ease of reference only one conduit 41*a* and two guide walls 42*a*, 42*b* are labelled. Exhaled air and the purging curtain of air pass to the inlet 46*a* of the conduit 41*a*. The walls 42*a*, 42*b* radiate from the central cavity of the valve assembly to the valve outlet 40*a* in a spiral manner. The spiralling nature of the conduit 41*a* increases the gaseous path length between the ambient atmosphere and the unidirectional valve mechanism 24, thus reducing the likelihood of unwanted increases of ambient gas. The cross section of the conduit 41*a* decreases the closer the conduit is to the ambient atmosphere. This accelerates exhaled air and purging air outwards, thus reducing the likelihood of unwanted ambient gas ingress. The exhaled and purging air exits each conduit via a small outlet 40*a*. The conduit 41*a* is shaped so as to turn any exhaled and purging air, and more importantly any incoming air, out of the plane of the spiral. This effectively turns the air through mutually perpendicular directions. This slows down any incoming air. The guide walls 42*a*, 42*b* are each provided with a radial projection 43*a*, 43*b* that slows any incoming air and helps to prevent a cyclonic motion of air from building-up within the valve assembly, should air be driven into the valve outlets. The use of multiple small valve outlets as opposed to one large vent decreases the risk of wind-blown ingress of ambient gas.

The curtain of air 22 may be provided continuously or during the inhalation process when ingress of contaminants is likely to occur.

Air deflector 28 may be provided with radically projecting vanes 47. These further help to prevent the build-up of cyclonic air motion with the valve assembly 20.

Figure 6:
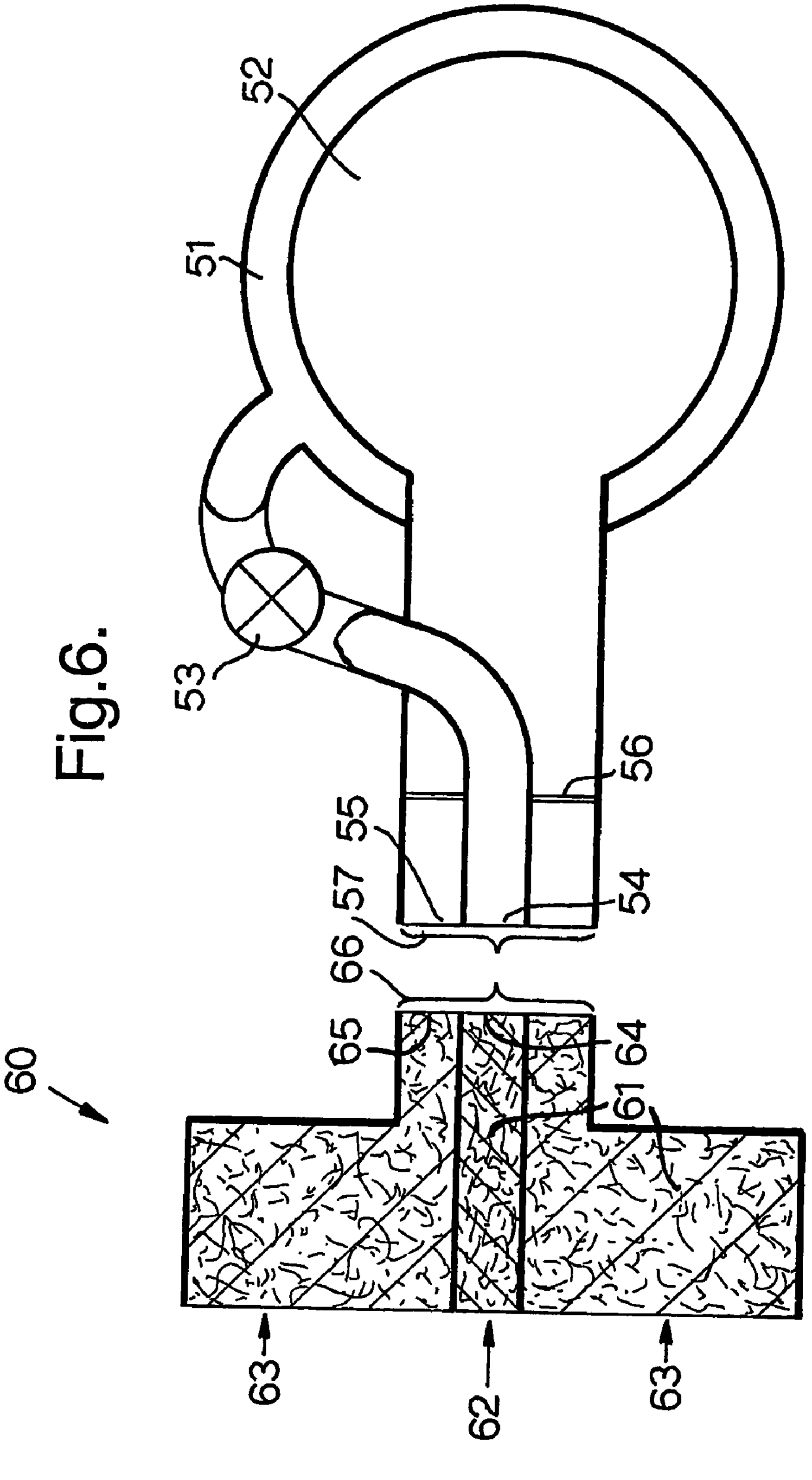
FIG. 6 shows a schematic block diagram of a respirator illustrating the first, third and fourth aspects of the present invention.

One arrangement of the respirator of the first embodiment of the present invention is shown in FIG. 6. The respirator air inlet 55 is, in use, in gaseous communication with the first cavity 52, thus forming a first gaseous pathway, a second air inlet 54 is in gaseous communication with the air pressure supply means 53 which is capable, in use, of providing gas to the second cavity 51, thus forming a second gaseous pathway, wherein the respirator and second air inlets are located in common filter connection means 57, and the filter connection means 57 is connectable to a suitably adapted filter 60 such that in use the first and second gaseous pathways are mutually isolated so that inhalation by the user does not substantially affect the pressure in the second gaseous pathway. Referring to FIG. 1, the first cavity 52 is formed between the first seal 7, the facepiece 1 and the face of the user. The second cavity 51 is formed between the second 6, the first seal 7 and a portion of the face of the user. A valve 56 is situated in the first gaseous pathway to prevent contaminated air from reaching the first cavity 52. The filter 60 has been adapted to mate with the respirator of the present invention. The filter 60 comprises first and second filter air inlets 62, 63, filtration material 61, first and second filter air outlets 64, 65 and respirator connection means 66. The first and second filter air outlets 64, 65 are located in a common respirator connection means 66. In use, air is drawn through the first filter air inlet 62, through the filtration material to the first filter air outlet 64. Air passes into the respirator vialt he second air inlet 54 into the second cavity 51. Similarly, air is drawn through the second filter air inlet 63, through the filtration material to the second filter air outlet 65. Inhaling air is drawn from the second filter air outlet 65 to the respirator air inlet 55 into the first cavity 52 and then into the lungs of the user. The gaseous pathway through the first filter air inlet to the first filter air outlet is isolated from that through the second filter air inlet to the second filter air outlet.

Thus, inhalation by the user does not affect the pressure in the second gaseous pathway and so the air pressure supply means 53 is not exposed to a drop in pressure and thus does not have to increase its energy consumption in order to maintain the required pressure in the second cavity 51.

The respirator connection means comprises a means for engaging with the safety interlock of an attached respirator (not shown) such that the air pressure supply means of the attached respirator may be actuated when the filter is properly fitted to the respirator. The filter to be fitted to the respirator may comprise suitable electrical contacts that mate with the contracts of the respirator so as to form a complete electrical circuit, thus permitting the air pressure supply means and thus the respirator to function. In the absence of the filter the air pressure supply means is left in open circuit mode and thus the air pressure supply means cannot operate.

The invention claimed is:

1. A valve assembly in a respirator comprising a valve body having a valve outlet portion and a valve inlet portion which together define a valve cavity for a valve mechanism permitting gas flow from the valve inlet portion to the valve outlet portion, an air purge means comprising a purge inlet, connectable to an air pressure supply means, an air purge outlet and an air deflection means in which the deflection means is spatially arranged relative to the valve mechanism and purge outlet so that, in use, air exiting the purge outlet and incident the air deflection means provides a curtain of air over the valve mechanism so as to inhibit exhaled and ambient air from flowing into the respirator; and in which the air purge means is configured so that the curtain of air is continuous when the purge inlet is connected to the air pressure supply means and the air pressure supply means is activated.

2. A valve assembly according to claim 1, in which the valve body is cylindrical in shape.

3. A valve assembly according to claim 1, in which the valve inlet portion provides a seat for the valve mechanism.

4. A valve assembly according to claim 3, in which the purge inlet and outlet is associated with the valve inlet portion.

5. A valve assembly according to claim 4, in which the deflection means is associated with the valve outlet portion.

6. A valve assembly according to claim 4, in which the purge outlet comprises one or more bores or channels in an upper surface of the valve inlet portion.

7. A valve assembly according to claim 6, in which the width of the bore or channel tapers inwardly towards to the valve outlet portion.

8. A valve assembly according to claim 4, in which the deflection means comprise a cylindrical boss or embossment on an inner surface of the valve outer portion.

9. A valve assembly according to claim 1, in which the outlet portion is associated with a dead-space protection member comprising air guide means.

10. A valve assembly according to claim 9, in which the air guide means comprise a plurality of vanes defining air conduits communicating with the purge outlet.

11. A valve assembly according to claim 10, in which the vanes extend toward the valve inlet portion to a greater extent at or adjacent the centre of the protection member than at its edge.

12. A valve assembly according to claim 9, in which the vanes inwardly turn to toward the centre of the protection member.

13. A valve assembly according to claim 9, in which the vane walls comprise inward radial protections or at adjacent the centre of the protection member.

14. A valve assembly according to claim 1, in which the valve mechanism comprises a membrane.

* * * * *